US005738133A

United States Patent [19]
Seki et al.

[11] Patent Number: 5,738,133
[45] Date of Patent: Apr. 14, 1998

[54] LIQUID ANALYZING APPARATUS

[75] Inventors: Kiwao Seki, Hitachinaka; Sadabumi Ohnuma, Hitachi, both of Japan

[73] Assignee: Hitachi, Ltd., Tokyo, Japan

[21] Appl. No.: 583,152

[22] Filed: Dec. 28, 1995

[30] Foreign Application Priority Data

Dec. 28, 1994 [JP] Japan ...................... 6-326632

[51] Int. Cl.⁶ .................... F16K 17/04; G01N 21/00
[52] U.S. Cl. .................. 137/115.26; 137/551; 73/864.84
[58] Field of Search .............. 137/115.26, 115.28, 137/551; 73/863.71, 864.84

[56] References Cited

U.S. PATENT DOCUMENTS

| 4,002,070 | 1/1977 | Howell | 73/863.71 X |
| 4,206,630 | 6/1980 | Powers | 73/864.84 |
| 4,791,950 | 12/1988 | Pedersen | 137/115.26 |
| 5,265,642 | 11/1993 | Buckminster et al. | 137/469 |

FOREIGN PATENT DOCUMENTS

| 0 158 776 | 10/1985 | European Pat. Off. |
| 6160271 | 6/1994 | Japan |

*Primary Examiner*—John Rivell
*Attorney, Agent, or Firm*—Kenyon & Kenyon

[57] ABSTRACT

In a liquid chromatographic analyzer apparatus, there is possibility that a flow cell is damaged when a flow passage is blocked and the inner pressure is increased. In order to prevent damage to the apparatus, liquid is prevented from leaking inside the apparatus. The liquid is discharged externally through a liquid discharging tube. A spring member is provided between the flow cell and the seal in a tube connecting portion to allow liquid to leak when the pressure is increased. Further, a light-proof tube for blocking light is connected to the flow cell to allow the leaked liquid to flow through the light-proof tube.

15 Claims, 7 Drawing Sheets

LIQUID ANALYZING APPARATUS

BACKGROUND OF THE INVENTION

The present invention relates to a liquid analyzing apparatus having a liquid analyzing flow cell such as a liquid chromatographic analyzer and a flow injection analyzer.

A common liquid chromatographic analyzer is constructed such that a liquid or a sample to be used for analysis is pumped using a pump having a high delivery pressure because a column of the liquid chromatographic analyzer has a large flow resistance.

A flow cell is connected in the downstream of the column to measure the separated sample.

However, there are some cases where the delivery pressure becomes so high due to change in various conditions that the column and the flow cell or the flow passage between them might be damaged.

In order to solve the disadvantage, an invention is disclosed in Japanese Patent Application Laid-Open No.6-160271 (1994). In Japanese Patent Application Laid-Open No.6-160271 (1994), a bypass flow passage having a flow control valve is provided in parallel to the flow passage connected to the flow cell. The pressure applied to the flow cell is then removed by controlling the flow control valve based on a value indicated a pressure gauge detector detecting the pressure from a liquid delivery means.

However, in a liquid chromatographic analyzer having a small liquid flow rate, the volume of the liquid flow passage between the column and the flow cell should be made small such that the delivered liquid to the liquid flow cell does not remain to suppress diffusion of the sample. Therefore, it is impossible to connect a protecting means against the occurrence of abnormal pressures such as a pressure gauge or a safety valve, as described in Japanese Patent Application Laid-Open No.6-160271, which increases the volume the flow passage.

That is, a means for detecting abnormality cannot be installed and the pressure increase due to the occurrence of abnormal pressure cannot be detected even when abnormal pressures occur. Therefore, there has been a problem in prevention which cause the flow cell or the tube to become damaged.

SUMMARY OF THE INVENTION

The present invention is to solve the above problems and to provide a liquid analyzing apparatus having a protecting means against the occurrence of abnormal pressures without increasing the volume of a flow passage.

A liquid analyzing apparatus comprising a liquid supplying passage, a liquid discharging passage, and a liquid flow passage. The liquid flow passage is formed by providing a liquid analyzing flow cell between the liquid supplying passage and the liquid discharging passage. A pressure release port is provided in the liquid flow passage which releases pressure from the liquid supplying passage with a pressing force exceeding a certain value determined by a maximum pressure applied by the liquid flow cell to the flow cell, the liquid supplying passage or the liquid discharging passage.

The liquid supplying passage or the liquid discharging passage is constructed in a two-layer structure, having an end portion of an outer layer is constructed to be liquid-proofed and end portion of an inner layer pushed to the flow cell using a spring member or the like.

Further, the outer layer of the liquid discharging passage is formed of a light-proof material.

Since a seal structure using the spring member is provided in a connecting mechanism between the flow cell and a tube or flow passage the liquid flowing in the flow passage is discharged from the connecting portion when the pressure is increased above an allowable value, therefore, it is possible to prevent the pressure from excessively increasing.

The tube is formed in a double tube structure. The tube in the outer layer is also connected to an outer wall of the flow cell to allow the discharged liquid to flow between the tube in the center and the tube in the outer side. By this construction, the discharged liquid can be conducted outside the analyzing apparatus together with the liquid flowing in the center tube.

In that case, by forming the tube in the outer side with a light-proof material, the light-proof function for the tube in the center can be obtained at the same time, and the number of tubes extending from the apparatus can be decreased.

In a liquid analyzing apparatus, in order to protect against damage to the flow cell or the tubes when the fluid flow resistance of the fluid flow passage is abnormally increased by the blockage of the fluid flow passage, a protection mechanism against the abnormal pressure can be utilized without increasing the volume of the fluid flow passage.

Even if liquid is discharged outside the flow cell while operating the protective function during an abnormal pressure, the liquid can be discharged outside the analyzing apparatus without internal leakage.

In an analyzing apparatus using light, it is necessary to block light from entering externally the apparatus. The tubes extending outside from the apparatus can be made light-proof, and the number of tubes can be minimized.

DETAILED DESCRIPTION

Initially, description will be made on an embodiment of an apparatus for performing absorptiometric analysis of liquid to which the present invention is applied.

Figure 1:
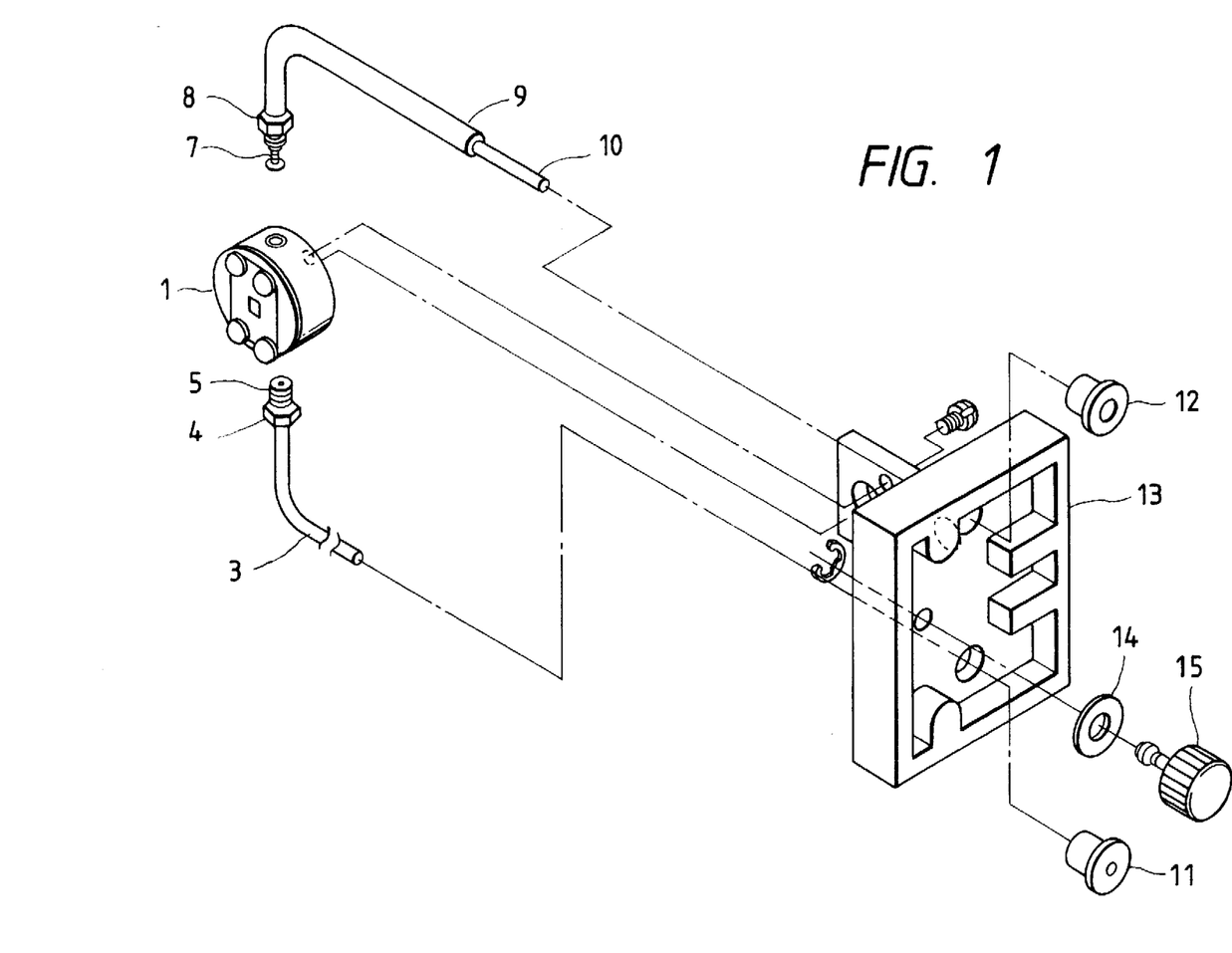
FIG. 1 is a view showing the construction of a cell in accordance with the present invention.

FIG. 1 is a view showing the construction of a cell unit 1 in accordance with the present invention. In an absorbance detector in liquid chromatographic apparatus, cell unit 1 is mounted in a spectroscope 20 as shown in FIG. 2, and has a function of conducting liquid flowing out from a tube 10 outside spectroscope 20 into the spectroscope 20 and allowing the liquid to flow a given distance in a light path.

Figure 2:
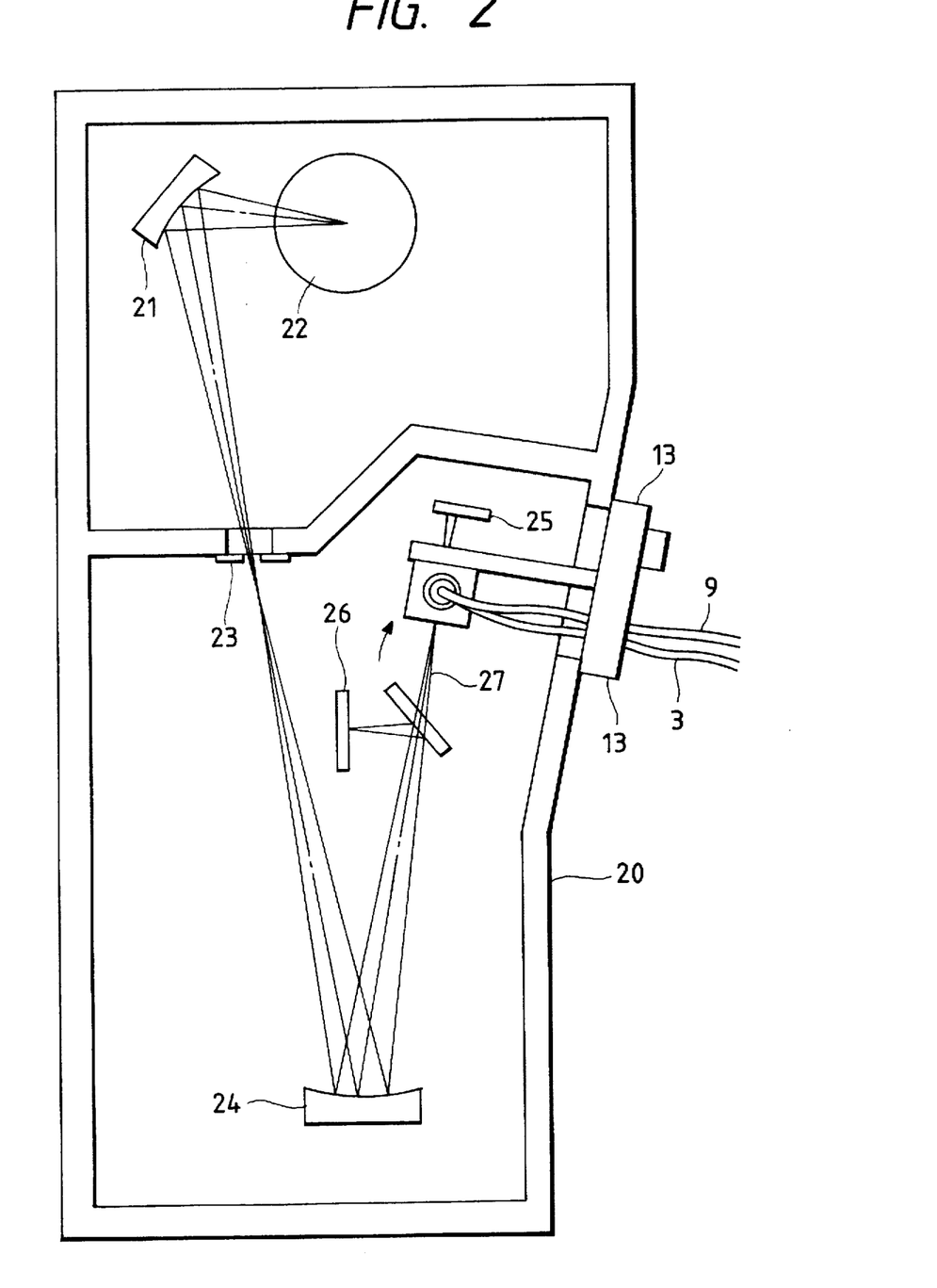
FIG. 2 is a view showing a spectroscopic analyzer to which the present invention is applied.

In FIG. 2, light emitted from a lamp 22 is gathered by a light-gathering mirror 21, and scattered into individual wavelengths by a diffraction grating 24 after passing through a slit 23. Then a part of the light enters into a light receiving element 26 to be directly converted into an electric signal. After passing through cell unit 1, the other light enters into a light receiving element 25 to be converted into an electric signal. By obtaining the ratio of the two electric signals, the light absorptivity of liquid flowing through the inside of a fluid flow cell in cell unit 1 is measured.

As is described above, in liquid chromatographic apparatus, it is necessary to conduct liquid existing externally into spectroscope 20 to be measured. Therefore, it is possible that liquid flows into cell unit 1 of spectroscope 20 through a liquid flow passage.

Since the liquid flows out to a waste liquid bottle (drain) outside spectroscope 20 through an outlet tube 10 after completion the light absorptivity measurement in cell unit 1, it is possible that light enters through a side of the flow passage.

Since the quantity of light is measured in spectroscope 20, external light must be prevented from entering spectroscope 20. Therefore, a light-proof tube 9 covers outlet tube 10 preventing external light from entering the spectroscope 20 through outlet tube 10 or a gap between outlet tube 10 and a packing 12. Further, by forming tubing in a two-layer structure (i.e. light-proof tube 9 and outlet tube 10), and consequently decreasing the number of tubes, the possibility of conducting external light to flow cell 30 is decreased. This contributes to decreasing the measurement error due to external light entering flow cell 30.

Although the two-layer structure, which is one of the characteristics of the present invention, is employed only in the outlet tube 10, it may also be employed in an inlet tube 2.

A light-proof tube 3 is constructed so that a seal member is tightened to the cell unit 1 using a screw 4 to prevent the liquid from leaking. Similarly, light-proof tube 9 is also constructed so that a seal member 6 is tightened to cell unit 1 using a screw 8 to prevent the liquid from leaking.

However, the outlet tube 10 contained in light-proof tube 9 is connected to flow cell 30 contained in the cell unit 1 through a spring 7 and seal member 6.

Figure 3:
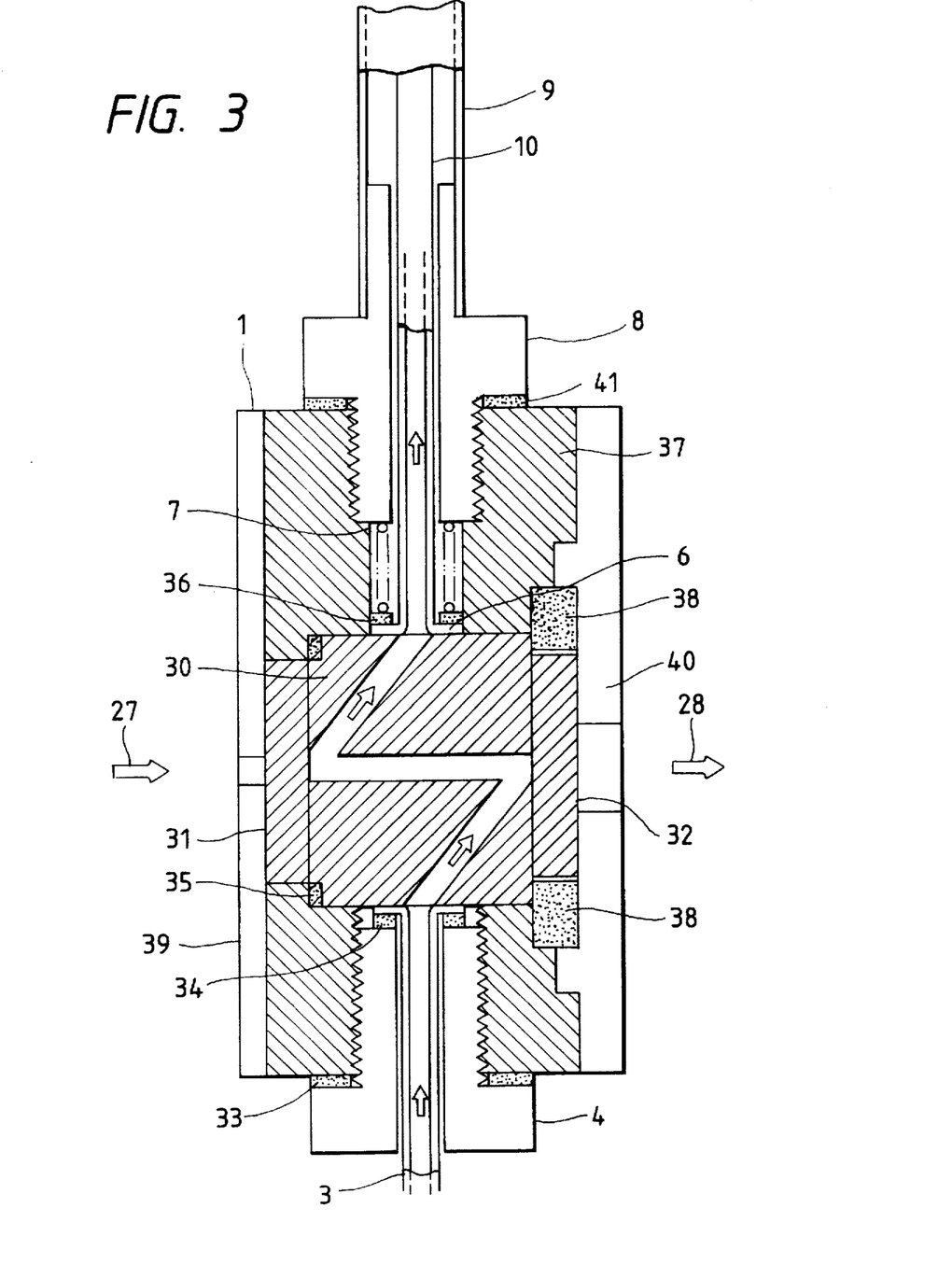
FIG. 3 is a detailed cross-sectional view showing the construction of a cell in accordance with the present invention.

FIG. 3 is an enlarged view of the flow cell 30 explaining the connections.

Flow cell 30 is closed with window plates 31 and 32 to form a light path. Flow cell 30 is mounted in a holder 37 and fixed to fixing plates 39 and 40 through a seals 35 and 38.

Light-proof tube 3 is tightly fixed to flow cell 30 with screw through a liquid-proof washer 34.

Screw 8 connecting light-proof tube 9 to cell 30 is connected to holder 37. An end portion of outlet tube 10 located in light-proof tube 9 is pushed towards flow cell 30 through washer 36 with spring 7 attached to screw 8 (hereinafter, this pushed portion is referred to as "seal portion 6").

Outlet tube 10 is tightly fixed to flow cell 30 with screw 8 through washer 36. Therefore, liquid flowing through inlet tube 2 does not leak through the light path in the cell but flows to the outlet tube 10.

Incident light 27 to cell until passes through the light path in flow cell 30 and goes out as an emitted light 28.

With the construction, when the pressure in flow cell 30 is abnormally increased, a gap is formed between seal portion 6 and flow cell 30 to leak the liquid, and consequently the cell unit 1 and tubes 2 and 10 are prevented from damage.

Light-proof tube 9 is connected to screw 8, and the leaked liquid, therefore, flows between light-proof tube 9 and outlet tube 10. The leaked liquid is conducted outside the spectroscope 20 without leaking into spectroscope 20. Since the outlet tube 10 is commonly connected to the waste liquid bottle (drain), the leaked liquid can be conducted to the waste liquid bottle (drain) by extending the light-proof tube 9 beyond outlet tube 10 without installing another tube. Since the leaked liquid does not leak into spectroscope 20 when liquid is leaked, degradation or fouling due to the leaked liquid does not occur in the optical system.

Figure 4:
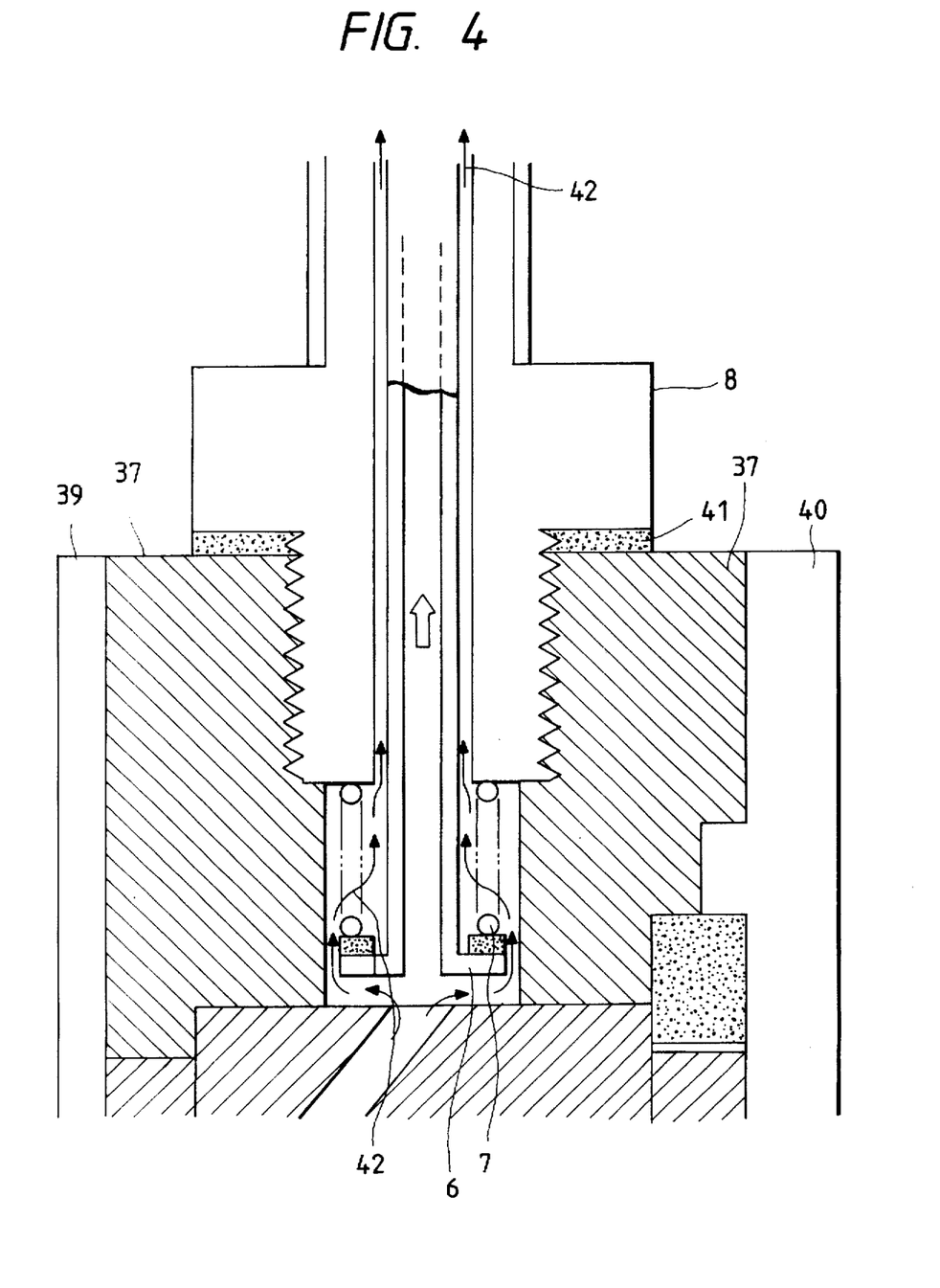
FIG. 4 is a detailed cross-sectional view showing a state where liquid flows out in a cell in accordance with the present invention.

FIG. 4 is an enlarged view of the vicinity of the seal portion 6.

When internal pressure of the flow passage is increased due to any abnormality, spring 7 is contracted and liquid leaks from the liquid flow passage between the cell holder 37 and seal portion 6 as shown in the figure. Since light-proof tube 9 is connected to screw 8, liquid 42 leaked around spring 7 flows between the light-proof tube 9 and outlet tube 10.

The space between light-proof tube 9 and outlet tube 10, to be called the second waste liquid passage, may be provided by using the two-layer tube structure as in the above embodiment, but may be also provided by arranging a new tube in addition to the existing waste liquid passages. As a detailed example, the connection portion of flow cell 30 and the new tube is constructed in the same manner as the above embodiment with the two-layer tube branched in a middle portion forming an inner layer space and an outer layer space. With this construction, by looking through which waste liquid passage of the two the waste liquid flows out, it is possible to judge whether an abnormal pressure is applied to the flow cell or not.

Further, with this construction, liquid 42 does not spill in the connecting portion of the flow cell 30 and the tubing where the liquid 42 is apt to leak by nature.

Although the above embodiment according to the present invention is applied to an absorbance detector, the same effects can be attained by applying the present invention to an fluorescent detector or a luminescent detector. Further, the same effects can be also attained by applying the present invention to an electric conductivity detector.

Figure 5:
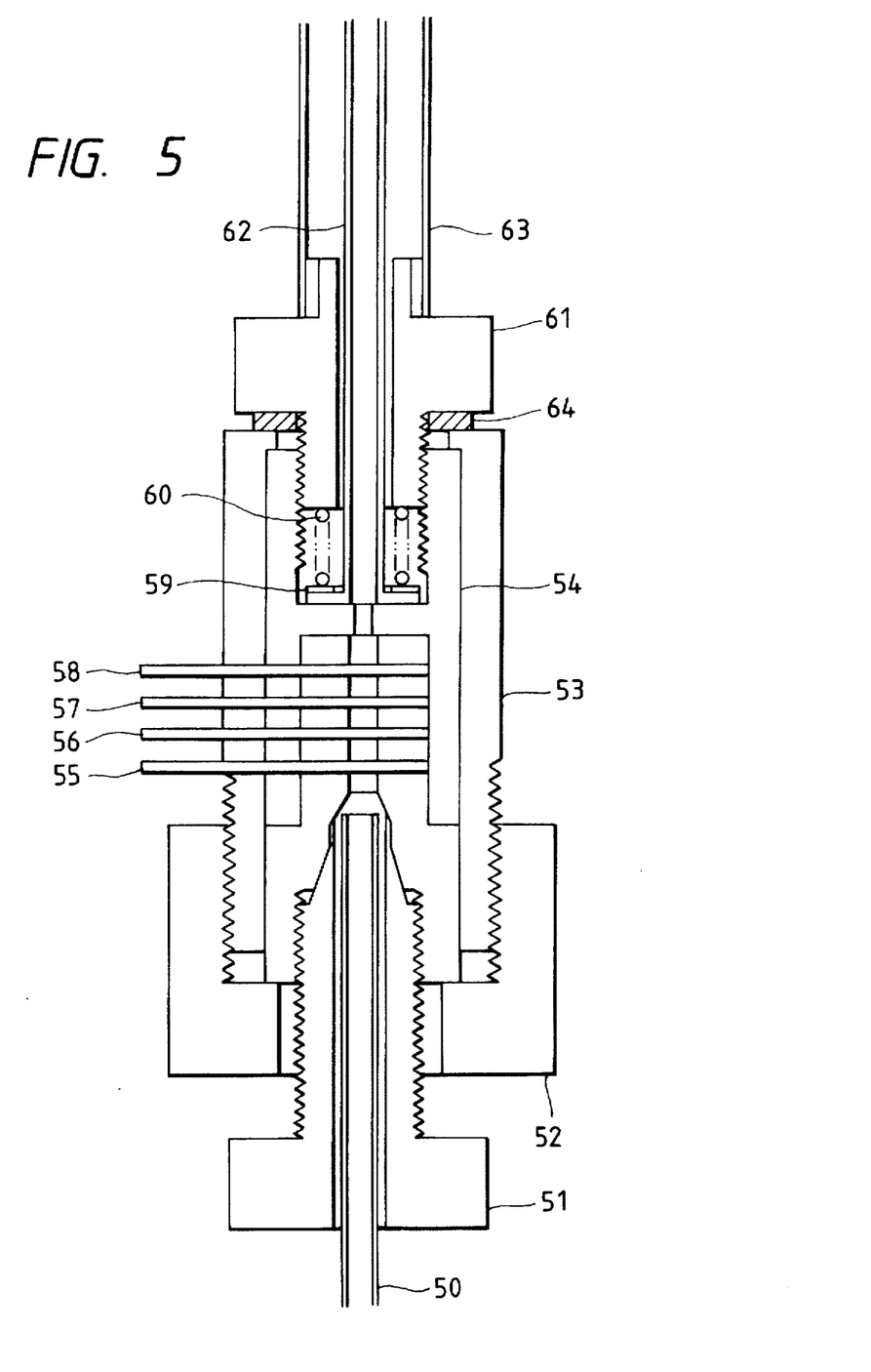
FIG. 5 is a view showing the construction of a cell in an electric conductivity detector to which the present invention is applied.

FIG. 5 shows a flow cell 53 in an electric conductivity detector to which the present invention is applied.

Liquid enters flow cell 53 through a light-proof tube 50, and the liquid after its electric conductivity is measured is directed to an outlet tube 62. The outlet tube 62 is tightly pushed to a cell body 54 with a spring 60. When the inner pressure of flow cell 53 is increased by any reason, the liquid is discharged through the tightly attached portion.

Since the outlet tube 62 is covered with a tube 63 and connected to a screw 61, leaked liquid flows between tube 62 and tube 63 to goes outside and does not leak inside the apparatus.

Figure 6:
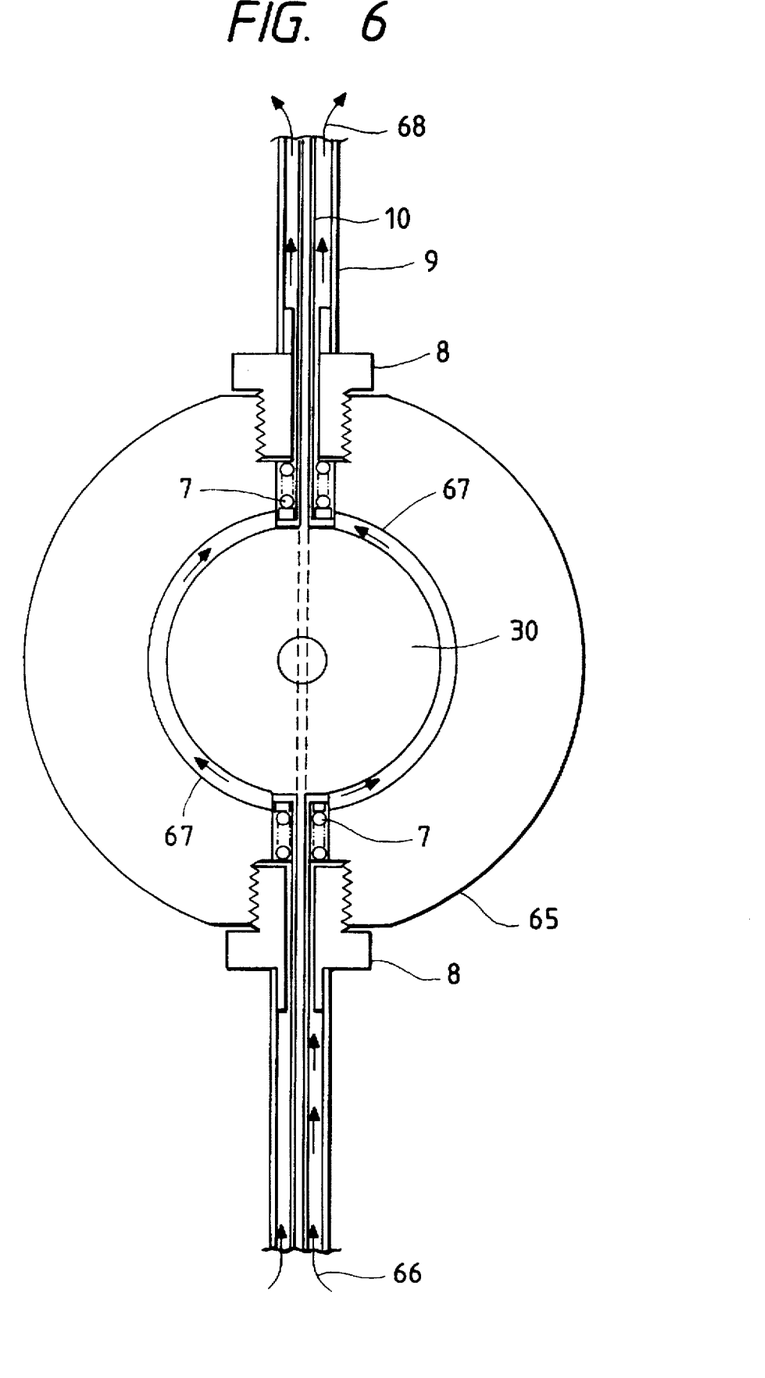
FIG. 6 is a view showing the construction of a cell having a cleaning function to which the present invention is applied.

Further, as shown in FIG. 6, two tubes in the inlet and in the outlet are formed in a double tube structure to use the passage between the center tube and the outer tube as a waste liquid flow passage, and both of the waste liquid flow passages are connected through a cell holder 65. With this construction, by allowing cleaning liquid 66 to flow from one end of the waste liquid flow passage, the cleaning liquid cleans the cell flow and the connecting portion and then flows outside. Therefore, the waste liquid flow passage and a spring mechanism can be cleaned from the outside without disassembling the cell flow.

Figure 7:
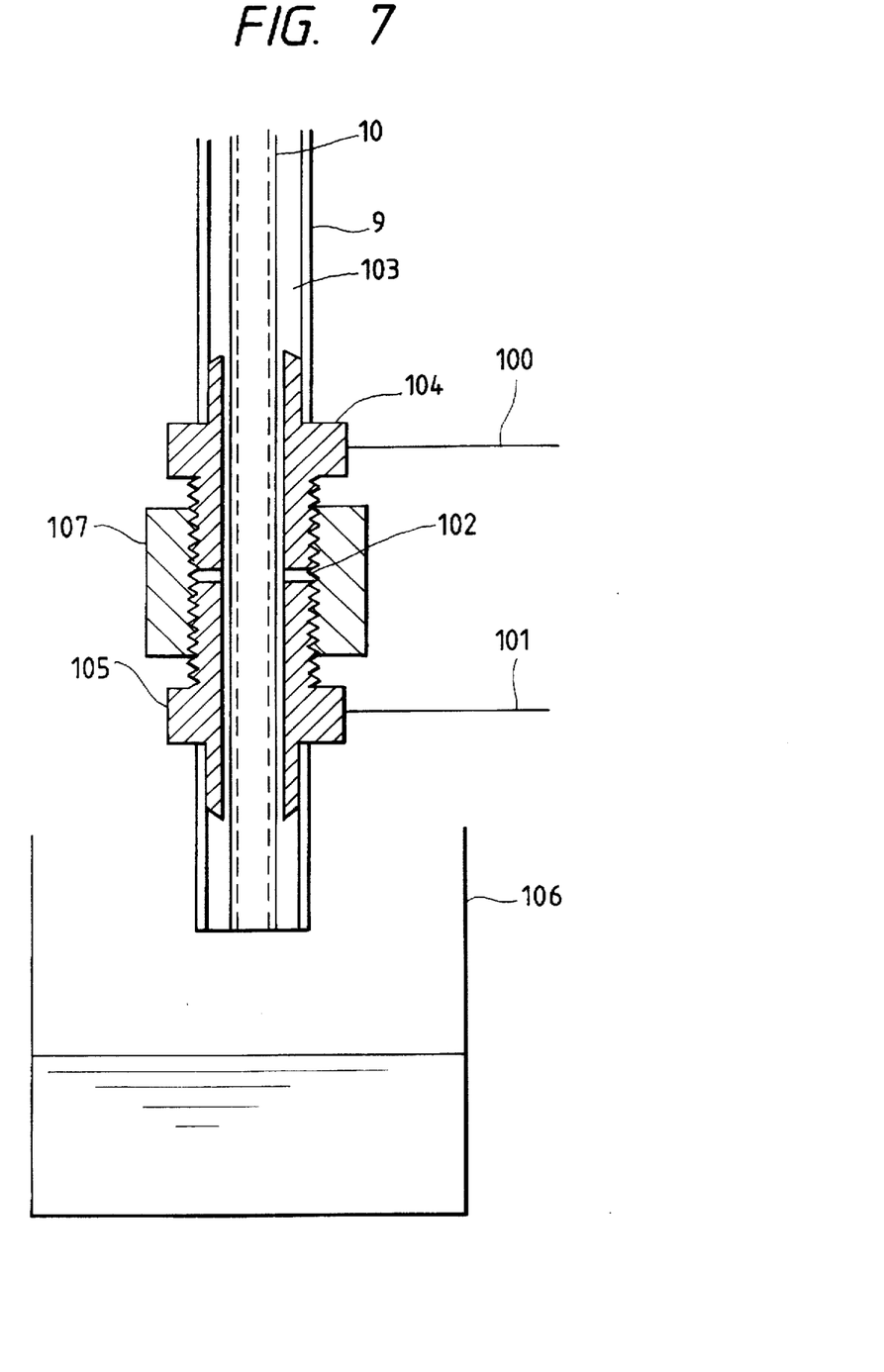
FIG. 7 is a view showing construction of a liquid discharging passage having an abnormal pressure detecting means in accordance with the present invention.

FIG. 7 is a view showing a detecting means for detecting whether liquid flows between the light-proof tube and the inlet tube or between the light-prof tube and the outlet tube.

In the embodiments described above, when pressure exceeding a certain pressure value is applied to the flow cell, the liquid is leaked between the light-proof tube and the inlet tube or the outlet tube in order to release the pressure exceeding the certain pressure value.

The embodiments according to the present invention described above are constructed in such that the leaked liquid does not spill over the measuring apparatus even if leakage of the liquid is large. In a case where the leakage of the liquid is extremely large, it is necessary to confirm the cause such as abnormality in the tube or blockage of the flow passage. However, in the above embodiment where the waste liquid flow tube has the two-layer structure, it is difficult to judge from which tube the liquid leaking, the inner or the outer because of using the light-proof tube.

The construction shown in FIG. 7 is to solve the problem. Conductive connectors 104, 105 connected to an electrode 100 and an electrode 101 respectively are arranged in the waste liquid flow passage 103 between light-proof tube 9 and outlet tube 10 through an insulator plate 102. A resistivity measuring means, not shown, is connected between the electrodes 100 and 101.

When liquid flows in the waste liquid flow passage in this structure, that is, when pressure is released to the second flow passage of the waste liquid flow passage in order to protect the flow cell, the electrodes 100 and 101 are conducted by the flowing waste liquid to react to the resistivity measuring means connected. With this reaction, it is possible to confirm the presence or absence of the waste liquid flow.

In a liquid chromatographic analyzer, liquid is pumped at several tens MPa because of using a column. However, the flow passage and the cell in the downstream of the column are generally constructed using materials not requiring pressure resistivity since the flow passage in the downstream of the column is in a low pressure. When an abnormal condition occurs in the downstream of the column, damage in the cell or the piping tubes cannot be avoided. However, according to the present invention, it is possible to prevent the damage since the construction can prevent pressure increase at occurrence of an abnormal condition. Further, in a conventional apparatus, when damage occurs in the flow passage, the inside of the spectroscope is fouled with the leaked liquid and the apparatus sometimes becomes out of use or is degraded in its performance. In the present invention, the leaked liquid can be easily conducted to a waste liquid bottle without leaking inside the spectroscope.

When the tube is broken, the liquid does not leak outside since the tube is formed in double tube structure. Therefore, the reliability is improved. Further, since these effects can be attained by not providing additional tubes, the construction can be made simple.

When leakage occurs, it is required to disassemble and clean the apparatus since the liquid is apt to crystalize at this leakage position. In the present invention, since the cleaning can be easily performed by merely allowing the cleaning liquid to flow through the waste liquid flowing passage, the maintenance can be easily performed.

What is claimed is:

1. A liquid analyzing apparatus comprising:
   a liquid supplying passage;
   a liquid discharging passage; and
   a liquid flow passage formed by providing a liquid analyzing flow cell between said liquid supplying passage and said liquid discharging passage; wherein a pressure release port is provided in said liquid flow passage, said pressure release port squeezing out pressure exceeding a certain value of pressure outside said liquid supplying passage with the pressing force of the pressure when the pressure exceeding the certain value of pressure is applied to said flow cell, said liquid supplying passage or said liquid discharging passage.

2. A liquid analyzing apparatus comprising:
   a liquid supplying passage;
   a liquid discharging passage; and
   a liquid flow passage formed by providing a liquid analyzing flow cell between said liquid supplying passage and said liquid discharging passage; wherein a pressure release valve is provided in said liquid supplying passage or said liquid discharging passage, said pressure release valve being forced to open by the pressure of liquid when said liquid is supplied at a pressure exceeding a certain value of pressure, to said flow cell.

3. A liquid analyzing apparatus comprising:
   a liquid supplying passage;
   a first liquid discharging passage; and
   a liquid flow passage formed by providing a liquid analyzing flow cell between said liquid supplying passage and said first liquid discharging passage; wherein a pressure release port is provided between said liquid supplying passage and a second liquid discharging passage, said pressure release port discharging liquid outside said liquid supplying passage with the force of pressure when the liquid having a pressure exceeding the certain value of pressure is applied to said flow cell, said liquid supplying passage or said liquid discharging passage.

4. A liquid analyzing apparatus comprising:
   a liquid supplying passage;
   a first liquid discharging passage; and
   a liquid flow passage formed by providing a liquid analyzing flow cell between said liquid supplying passage and said first liquid discharging passage; wherein a pressure release port is provided between said liquid supplying passage and a second liquid discharging passage having a pressure lower than the pressure in said liquid flow passage, said pressure release port squeezing out pressure outside said liquid supplying passage with the force of pressure when a pressure exceeding a certain value of pressure is applied to said flow cell, said liquid supplying passage or said liquid discharging passage.

5. A liquid analyzing apparatus according to claim 1, wherein said certain value of pressure is lower than a withstanding pressure of said liquid analyzing flow cell.

6. A liquid analyzing apparatus comprising:
   a liquid supplying passage;
   a liquid discharging passage having a two-layer structure; and
   a liquid flow passage formed by providing a liquid analyzing flow cell between said liquid supplying passage and said liquid discharging passage, wherein a pressure release port is provided in an inner layer of said liquid discharging passing having a two-layer structure, said pressure release port releasing pressure exceeding a certain value of pressure with the force of pressure when the pressure exceeding the certain value of pressure is applied to said flow cell, said liquid supplying passage or said liquid discharging passage.

7. A liquid analyzing apparatus comprising:
   a liquid supplying passage having a two-layer structure;

a liquid discharging passage; and a liquid flow passage formed by providing a liquid analyzing flow cell between said liquid supplying passage and said liquid discharging passage; wherein a pressure release port is provided in an inner layer of said liquid supplying passage having the two-layer structure, said pressure release port releasing pressure exceeding a certain value of pressure with the force of pressure when the pressure exceeding the certain value of pressure is applied to said flow cell, said liquid supplying passage or said liquid discharging passage.

8. A liquid analyzing apparatus according to claim 6, wherein said certain value of pressure is lower than a withstanding pressure of said liquid analyzing flow cell.

9. A liquid analyzing apparatus comprising:

a liquid supplying passage;

a liquid discharging passage having a two-layer structure; and a liquid flow passage formed by providing a liquid analyzing flow cell between said liquid supplying passage and said liquid discharging passage;

wherein a portion between an end portion of an outer layer of said liquid discharging passage having the two-layer structure and said liquid analyzing flow cell are kept liquid-proof; and a spring member being arranged fixed to said end portion of the outer layer such that the spring member pushes said end portion of the inner layer to said liquid analyzing flow cell.

10. A liquid analyzing apparatus comprising:

a liquid supplying passage having a two-layer structure;

a liquid discharging passage;

a liquid flow passage formed by providing a liquid analyzing flow cell between said liquid supplying passage and said liquid discharging passage, wherein a portion between an end portion of an outer layer of said liquid supplying passage having the two-layer structure and said liquid analyzing flow cell are kept liquid-proof; and a spring member being arranged fixed to said end portion of the outer layer such that the spring member pushes said end portion of the inner layer to said liquid analyzing flow cell.

11. A liquid analyzing apparatus comprising:

a liquid supplying passage having a two-layer structure;

a liquid discharging passage having a two-layer structure;

a liquid flow passage formed by providing a liquid analyzing flow cell between said liquid supplying passage and said liquid discharging passage, wherein a portion between an end portion of an outer layer of said liquid supplying passage having the two-layer structure and said liquid analyzing flow cell are kept liquid-proof; and a spring member being arranged fixed to said end portion of the outer layer such that the spring member pushes said end portion of the inner layer to said liquid analyzing flow cell.

12. A liquid analyzing apparatus according to claim 6 further including:

a plurality of electrodes kept in an insulating state from one another are arranged between the inner layer and the outer layer of said liquid supplying passage having the two-layer structure or said liquid discharging passage having a two-layer structure and means for measuring the resistivity between each electrodes provided in each of said plurality of electrodes.

13. A liquid analyzing apparatus having a liquid analyzing flow cell, comprising:

a tube connecting mechanism having a seal mechanism using a spring member provided in a liquid outlet of a flow cell and/or a liquid inlet of a flow cell, liquid being discharged through said tube connecting mechanism when a pressure in the flow cell becomes above a pressure determined by said spring member.

14. A liquid analyzing apparatus according to claim 13, wherein a tube connected to said tube connecting mechanism has a double tube structure: liquid to be analyzed flowing in the inner tube and discharged liquid flowing at an elevated pressure between said inner tube and the outer tube.

15. A liquid analyzing apparatus according to claim 14, wherein the outer layer portion of said tube is made of a light-proof material.

* * * * *

UNITED STATES PATENT AND TRADEMARK OFFICE
CERTIFICATE OF CORRECTION

PATENT NO. : 5,738,133
DATED : 14 April 1998
INVENTOR(S) : Kiwao SEKI et al.

It is certified that error appears in the above-identified patent and that said Letters Patent is hereby corrected as shown below:

| Column | Line | |
|---|---|---|
| 1 | 26 | After "indicated" insert --by--. |
| 1 | 36 | After "volume" insert --of--. |
| 1 | 42 | Change "cause" to --causes--. |
| 1 | 63 | After "outer layer" delete "is". |
| 1 | 64 | Change "proofed" to --proof-- before "end" insert --an-- |
| 2 | 19 | Before "tubes" insert --fluid--; before "flow" delete "fluid". |
| 2 | 30 | Delete "externally"; after "apparatus" insert --from the outside--. |

UNITED STATES PATENT AND TRADEMARK OFFICE
CERTIFICATE OF CORRECTION

PATENT NO. : 5,738,133
DATED : 14 April 1998
INVENTOR(S) : Kiwao SEKI et al.

It is certified that error appears in the above-identified patent and that said Letters Patent is hereby corrected as shown below:

| Column | Line | |
|---|---|---|
| 2 | 43 | Change "out in a cell" to --out of a cell--. |
| 2 | 61 | Before "cell" insert --a--. |
| 3 | 16 | After "completion" insert --of--. |
| 3 | 24 | After "forming" insert --the--. |
| 3 | 41 | Change "in the cell unit 1" to --in cell unit 1--. |
| 3 | 47 | Before "seals" delete "a". |
| 3 | 61 | Change "until" to --unit 1--. |
| 4 | 3 | After "outside" delete "the". |
| 4 | 4 | After "Since" delete "the". |
| 4 | 7 | After "extending" delete "the". |
| 4 | 14 | Before "liquid" insert --the--. |

UNITED STATES PATENT AND TRADEMARK OFFICE
CERTIFICATE OF CORRECTION

PATENT NO. : 5,738,133

DATED : 14 April 1998

INVENTOR(S) : Kiwao SEKI et al.

It is certified that error appears in the above-identified patent and that said Letters Patent is hereby corrected as shown below:

| Column | Line | |
|---|---|---|
| 4 | 15 | After "between" delete "the". |
| 4 | 18 | After "between" delete "the". |
| 4 | 48 | Change "by any reason" to --for any reason--. |
| 4 | 52 | Change "goes" to --go--. |
| 4 | 67 | Change "light-prof" to --light-proof--. |
| 5 | 7 | After "such" insert --a way--. |
| 5 | 14 | After "liquid" insert --is--. |
| 5 | 15 | After "inner" insert --tube--; after "outer" insert --tube--. |
| 5 | 36 | Change "in a" to --at a--. |
| 5 | 43 | Change "out of" to --non-functional--. |
| 5 | 44 | Delete "use". |

UNITED STATES PATENT AND TRADEMARK OFFICE
CERTIFICATE OF CORRECTION

PATENT NO. : 5,738,133

DATED : 14 April 1998

INVENTOR(S) : Kiwao SEKI et al.

It is certified that error appears in the above-identified patent and that said Letters Patent is hereby corrected as shown below:

| Column | Line | |
|--------|------|---|
| 6 | 48 | After "according" insert --to--. |
| 6 | 60 | Change "passing" to --passage--. |

Signed and Sealed this

Eighteenth Day of May, 1999

Attest:

Attesting Officer

Q. TODD DICKINSON

Acting Commissioner of Patents and Trademarks